US010878512B1

(12) United States Patent
Al-Zoubi et al.

(10) Patent No.: US 10,878,512 B1
(45) Date of Patent: Dec. 29, 2020

(54) BLOCKCHAIN TECHNOLOGY FOR STORING ELECTRONIC MEDICAL RECORDS TO ENABLE INSTANT LIFE INSURANCE UNDERWRITING

(71) Applicant: United Services Automobile Association (USAA), San Antonio, TX (US)

(72) Inventors: Amjed Ratib Al-Zoubi, Northville, MI (US); Meliza Carrion, San Antonio, TX (US); Joseph George, Bee Cave, TX (US); Christopher Scott Lowe, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 0 days.

(21) Appl. No.: 16/057,483

(22) Filed: Aug. 7, 2018

Related U.S. Application Data

(60) Provisional application No. 62/542,063, filed on Aug. 7, 2017.

(51) Int. Cl.
| | |
|---|---|
| *G06Q 40/08* | (2012.01) |
| *G06Q 30/06* | (2012.01) |
| *H04L 9/06* | (2006.01) |
| *G06F 21/62* | (2013.01) |
| *G06F 16/182* | (2019.01) |

(Continued)

(52) U.S. Cl.
CPC .......... *G06Q 40/08* (2013.01); *G06F 16/182* (2019.01); *G06F 16/1805* (2019.01); *G06F 16/9535* (2019.01); *G06F 21/6245* (2013.01); *G06Q 30/0641* (2013.01); *H04L 9/0637* (2013.01); *H04L 2209/38* (2013.01).

(58) Field of Classification Search
CPC ................ G06Q 40/08; G06Q 30/0641; G06F 16/9535; G06F 16/1805; G06F 16/182; G06F 21/6245; H04L 9/0637; H04L 2209/38
USPC .......................................................... 705/4
See application file for complete search history.

(56) References Cited

U.S. PATENT DOCUMENTS

| | | | | |
|---|---|---|---|---|
| 7,814,006 | B1 * | 10/2010 | Solis et al. ............. | G06Q 40/00 |
| | | | | 705/38 |
| 10,366,204 | B2 * | 7/2019 | Tanner, Jr. et al. ... | G06F 19/328 |
| | | | | 21/645 |

(Continued)

OTHER PUBLICATIONS

Accenture, Editing the Undeitable Blockchain, Why distributed Ledger Technology Must Adapt to an Imperfect World, https://www.accenture.com/_acnmedia/pdf-33/accenture-editing-uneditable-blockchain.pdf#zoom=50 (2016). (Year: 2016).*

(Continued)

*Primary Examiner* — Elizabeth H Rosen
*Assistant Examiner* — George N. Proios
(74) *Attorney, Agent, or Firm* — Fletcher Yoder, PC

(57) ABSTRACT

Systems and methods for using blockchain data for automated underwriting and product issuance are provided. A request is received, via a website, for a personalized quote for a product. The requestor is identified and blockchain data related to the requestor is gathered. The blockchain data includes data pertinent to the personalized quote. The personalized quote is determined based at least in part upon the gathered blockchain data. The personalized quote is then presented via the website.

20 Claims, 10 Drawing Sheets

(51) Int. Cl.
*G06F 16/18* (2019.01)
*G06F 16/9535* (2019.01)

(56) References Cited

U.S. PATENT DOCUMENTS

| | | | | |
|---|---|---|---|---|
| 2011/0040582 | A1* | 2/2011 | Mullins | G06Q 40/00 |
| | | | | 705/4 |
| 2012/0232935 | A1* | 9/2012 | Voccola | G06Q 40/00 |
| | | | | 705/4 |
| 2012/0316893 | A1* | 12/2012 | Egawa | G06Q 50/22 |
| | | | | 705/2 |
| 2018/0285979 | A1* | 10/2018 | Chessell et al. | G06Q 40/08 |
| | | | | 40/8 |
| 2018/0342018 | A1* | 11/2018 | Pancholi et al. | G06Q 40/08 |
| | | | | 3/482 |
| 2019/0057226 | A1* | 2/2019 | Arbutina | G06F 21/64 |

OTHER PUBLICATIONS

AICPA, Blockchain Technology and Its Potential Impact on the Audit and Assurance Profession,https://www.aicpa.org/content/dam/aicpa/interestareas/frc/assuranceadvisoryservices/downloadabledocuments/blockchain-technology-and-its-potential-impact-on-the-audit-and-assurance-profession.pdf (2017). (Year: 2017).*

* cited by examiner

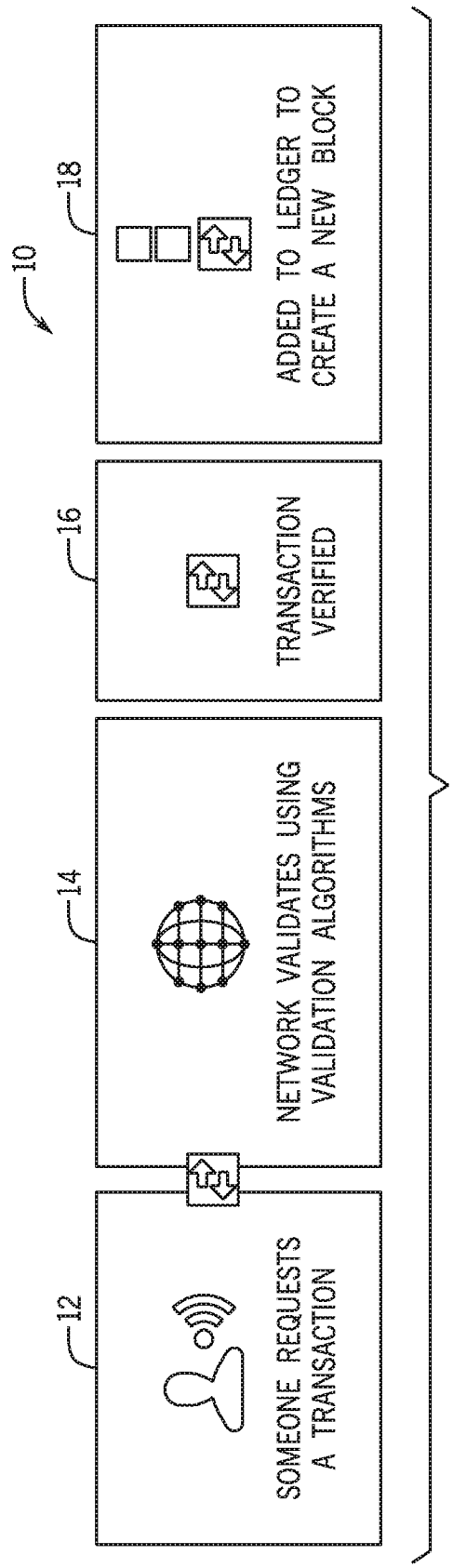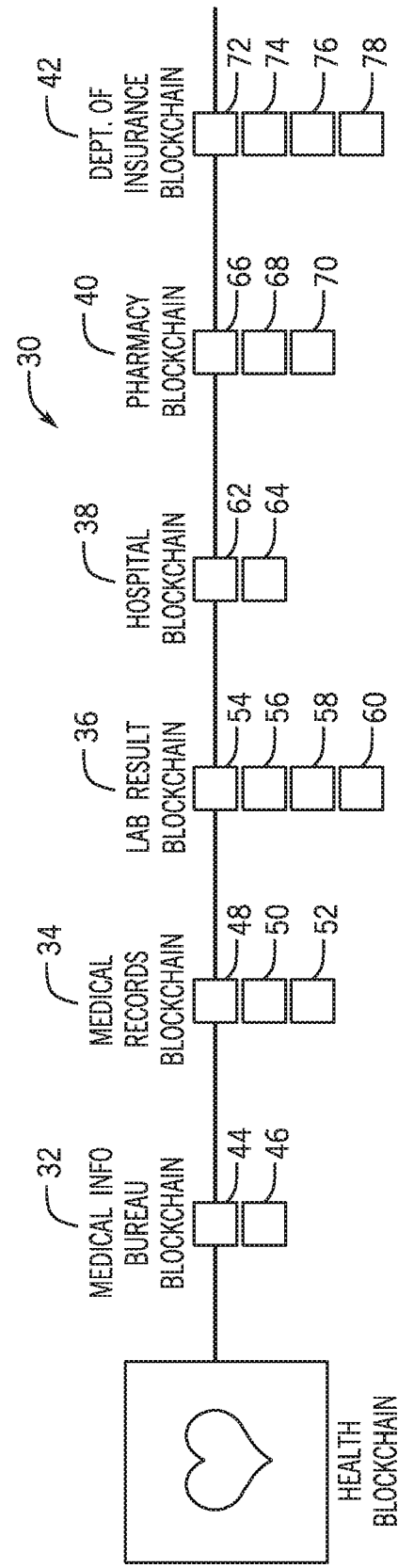

```
                                              ┌─ 190
    ┌─────────────────────────────────────┐
    │  UNDERWRITING REQUESTS              │
192─┼─ IDENTITY                      ✓    │
194─┼─ DIGITAL CURRENCY                   │
196─┼─ INVESTMENTS                        │
198─┼─ CASH                               │
200─┼─ CARDS                              │
202─┼─ SOCIAL MEDIA                  ✓    │
204─┼─ CREDIT                             │
206─┼─ HEALTH                        ✓    │
    │     MEDICAL RECORDS                 │
    │     LAB RESULTS                     │
    │     HOSPITAL                        │
    │     PHARMACY                        │
    │     MIB (MEDICAL INFORMATION BUREAU)│
    │     TEXAS DEPARTMENT OF INSURANCE   │
    │  208─[ DECLINE ]   [ AGREE ]─210    │
    └─────────────────────────────────────┘
```

FIG. 6

| CO 2 | MY USAA  MY TOOLS  PRODUCTS  ADVICE  CLAIMS  HELP  🔍 | SIGNED IN AS JOHN SMITH |

— 290

JOHN SMITH
1234 ANYWHERE,
SAN ANTONIO, TX 78261
⊘ – MEDICAL INFORMATION BUREAU
⊘ – DEPARTMENT OF DEFENSE, AIR FORCE
⊘ – IDENTIFICATION

262 —
$250K | TERM LIFE | 30 YRS
$40.37
MONTHLY PREMIUM

— 236

234 — 234

MEMBERSHIP AND ITS BENEFITS | YOU ARE ELIGIBLE FOR OTHER PRODUCTS AS WELL.

| 🚗 AUTO EXPERIENCE | 🏠 THE HOME TEAM | 💰 BANKING & SAVINGS | ☸ INVESTMENTS | 💳 CREDIT CARD |
| 294E | 294D | 294C | 294B | 294A |

— 294

APPLICATION VERIFICATION  — 292

FULL NAME
[JOHN SMITH]

DATE OF BIRTH
[NOVEMBER 2, 1984]

MAILING ADDRESS
[1234 ANYWHERE, SAN ANTONIO, TX 78261]

PHYSICAL ADDRESS
[1234 ANYWHERE, SAN ANTONIO, TX 78261]

CELL PHONE
[(210) 334-2074]

WORK PHONE
[(210) 567-1234]

DRIVER'S LICENSE
[TX DL #02286354]

EMAIL ADDRESS
[JOHN.SMITH@ME.COM]

EXISTING POLICIES

DO YOU CURRENTLY OWN ANY LIFE INSURANCE OR ANNUITY PRODUCTS?   ○ YES  ⦿ NO
DO YOU CURRENTLY HAVE ANY PENDING LIFE INSURANCE POLICIES?   ○ YES  ⦿ NO

[ YES, THIS IS CORRECT ] — 296

FIG. 9

Figure 10:
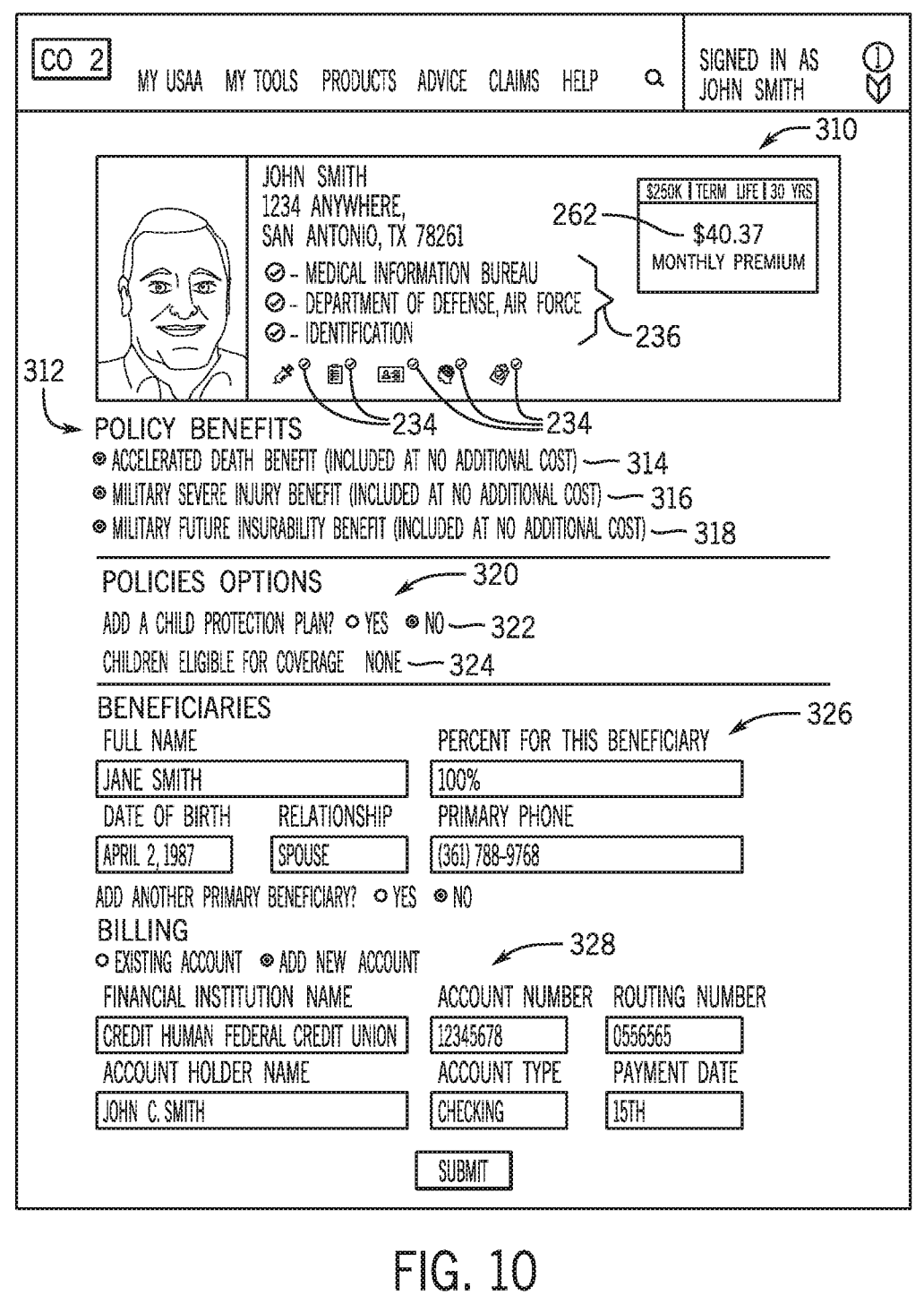

| CO 2 | MY USAA   MY TOOLS   PRODUCTS   ADVICE   CLAIMS   HELP   🔍 | SIGNED IN AS JOHN SMITH |

310

JOHN SMITH
1234 ANYWHERE,
SAN ANTONIO, TX 78261
262
⊘ - MEDICAL INFORMATION BUREAU
⊘ - DEPARTMENT OF DEFENSE, AIR FORCE
⊘ - IDENTIFICATION $250K | TERM LIFE | 30 YRS
$40.37
MONTHLY PREMIUM

236

312 → POLICY BENEFITS —234— —234—
● ACCELERATED DEATH BENEFIT (INCLUDED AT NO ADDITIONAL COST) — 314
● MILITARY SEVERE INJURY BENEFIT (INCLUDED AT NO ADDITIONAL COST) — 316
● MILITARY FUTURE INSURABILITY BENEFIT (INCLUDED AT NO ADDITIONAL COST) — 318

POLICIES OPTIONS — 320
ADD A CHILD PROTECTION PLAN?   ○ YES   ● NO — 322
CHILDREN ELIGIBLE FOR COVERAGE   NONE — 324

BENEFICIARIES — 326
FULL NAME | PERCENT FOR THIS BENEFICIARY
[JANE SMITH] | [100%]
DATE OF BIRTH | RELATIONSHIP | PRIMARY PHONE
[APRIL 2, 1987] | [SPOUSE] | [(361) 788-9768]
ADD ANOTHER PRIMARY BENEFICIARY?   ○ YES   ● NO

BILLING — 328
○ EXISTING ACCOUNT   ● ADD NEW ACCOUNT
FINANCIAL INSTITUTION NAME | ACCOUNT NUMBER | ROUTING NUMBER
[CREDIT HUMAN FEDERAL CREDIT UNION] | [12345678] | [0556565]
ACCOUNT HOLDER NAME | ACCOUNT TYPE | PAYMENT DATE
[JOHN C. SMITH] | [CHECKING] | [15TH]

[SUBMIT]

BLOCKCHAIN TECHNOLOGY FOR STORING ELECTRONIC MEDICAL RECORDS TO ENABLE INSTANT LIFE INSURANCE UNDERWRITING

CROSS-REFERENCE TO RELATED APPLICATION

This application claims priority to and the benefit of U.S. Provisional Application No. 62/542,063, entitled "BLOCKCHAIN TECHNOLOGY FOR STORING ELECTRONIC MEDICAL RECORDS TO ENABLE INSTANT LIFE INSURANCE UNDERWRITING," filed Aug. 7, 2017, which is hereby incorporated by reference in its entirety for all purposes.

BACKGROUND

The present disclosure relates generally to healthcare tracking via blockchain technologies. More specifically, the present disclosure relates to using healthcare blockchain technology to perform automated underwriting.

Underwriting is an extremely detail intensive process in which insurance providers and their members utilize significant time and resources to verify health information indicative of risk that may impact an insurance quote. For example, today, medical records and other pertinent health data is processed via hard copies of documents (e.g., paper versions). This makes data capture and analysis quite tedious. Further, when digitized, the documents are oftentimes unsearchable and still require manual data entry from the digitized documents. Further, while a significant amount of time any effort may be provided in the underwriting process, certain pertinent health information may be missed by this highly-involved process, especially considering the multitude of sources of this health information. Accordingly, new techniques useful for accurate and efficient underwriting is desirable.

DRAWINGS

These and other features, aspects, and advantages of the present disclosure will become better understood when the following detailed description is read with reference to the accompanying drawings in which like characters represent like parts throughout the drawings, wherein:

FIG. 1 is a flowchart that illustrates a process for generating ledger entries using blockchain, in accordance with an embodiment.

FIG. 2 is a schematic diagram of a health blockchain, in accordance with an embodiment;

FIG. 6 is a schematic diagram of a graphical user interface for permitting access to components of a blockchain wallet for underwriting purposes, in accordance with an embodiment;

FIG. 9 is a schematic diagram, illustrating a graphical user interface (GUI) for providing an auto-populated application for the personalized service, in accordance with an embodiment;

FIG. 10 is a schematic diagram, illustrating a graphical user interface (GUI) for providing personalized service options, in accordance with an embodiment.

DETAILED DESCRIPTION

Figure 3:
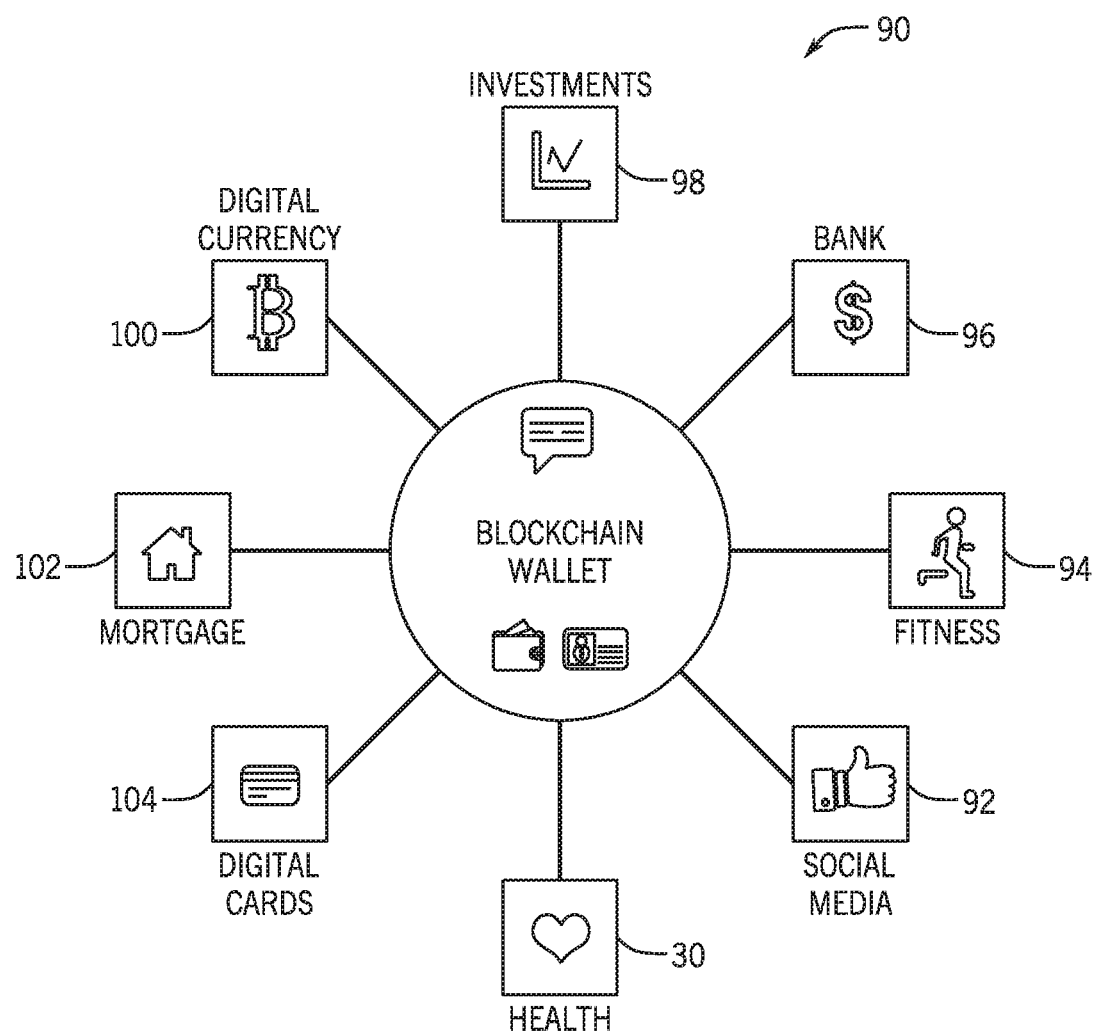
FIG. 3 is a schematic diagram illustrating a blockchain wallet, in accordance with an embodiment.

One or more specific embodiments of the present disclosure are described above. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments are generally directed toward new techniques for insurance underwriting. By utilizing blockchain technology, the underwriting process may become more efficient, resulting in a significant cost reduction, reduction in manual underwriting tasks, and enhanced user control during the underwriting process, along with many additional benefits.

As mentioned above, when quoting an insurance policy, insurance companies have typically performed manual underwriting processes to assess health and/or lifestyle information for the potential insured. This health and/or lifestyle information may be used to assess risk for insuring the potential insured, which results in quoted premium (e.g., wherein increased risk results in higher premiums). Unfortunately, however, it may be quite burdensome to manually gather and analyze this information. Further, information may be lacking, as relevant sources of data may be missed or ignored.

The current techniques relate to using blockchain data to track health information (e.g., health history, medical records, etc.). The blockchain data may be accessed by insurance provider computers to access and automate at least a portion of the underwriting process.

Blockchain is an incorruptible digital ledger that is distributed and can be programmed to record digital transactions. By allowing digital information to be distributed but not copied, blockchain technology provides ease of access to digital data, while not being easily corrupted. While blockchain implementations may cover different scopes, from infrastructure, generic platforms to specific applications, a blockchain solution generally builds on a set of four characteristics: decentralized validation, redundancy, immutable storage, and encryption. FIG. 1 is a flowchart that illustrates a process 10 for generating ledger entries using blockchain, in accordance with an embodiment.

The process 10 begins by someone requests a transaction (block 12). For example, when a particular patient receives treatment, a doctor/hospital may request to publish a medical record regarding the patient. Other examples might include a request to publish prescriptions of a patient, a request to publish lab results of a patient, etc.

Upon submission of the request for a blockchain transaction, the network (e.g., the blockchain provision services) may validate the transaction (block 14). For example, the validation may include determining whether the requestor is valid submitter of information to the blockchain. Thus, only certified entities may publish to the blockchain, while non-authorized entities may not publish to the blockchain. Examples of valid entities may be a doctor, a pharmacy, a hospital, an emergency clinic, etc. Further, the validation may determine whether the transaction data is valid for publication on the blockchain. For example, the verification process may determine whether the transaction applies to data only applicable to a certain sex and find the transaction invalid if the patient is not that certain sex.

Once the transaction has been verified, the data provided in the transaction request is added as a ledger entry in the blockchain (block 18). For example, results of a patient's checkup, a prescription afforded the patient, and/or lab results of the patient, etc. may be published to the patient's health blockchain. The data is added by creating a new block in the blockchain.

The blockchain may be accessed by authorized users for retrieval of health information. For example, when the patient is receiving treatment at a hospital, an agent of the hospital may access the patient's blockchain to determine characteristics of the patient that may be prudent to the treatment. For example, the health blockchain may provide an indication of allergies of the patient, current or historical prescriptions of the patient, historical medical treatments, etc.

FIG. 2 is a schematic diagram of a health blockchain 30, in accordance with an embodiment. In the current embodiment, the health blockchain 30 is an aggregation of separate blockchains. For example, in the current embodiment, the aggregation includes a Medical Information Bureau ("MIB Group") blockchain 32, a Medical Records blockchain 34, a Lab Results blockchain 36, a Hospital blockchain 38, a Pharmacy blockchain 40, and a Department of Insurance blockchain 42. In alternative embodiments, the health blockchain 30 may be less granular, aggregating blocks rather than sub-blockchains.

The MIB Group is a membership corporation owned by approximately 430 member insurance companies in the United States and Canada. The MIB Group provides services designed to protect insurers, policyholders, and applicants from attempts to conceal or omit information material to underwriting life and health insurance. MIB's data base does not contain actual medical records and information is gathered from an underwriting investigation that may include: information from the applicant's medical questionnaire (application), relevant information from the applicant's attending physician, notice of adverse lab test results (non-specific flag as to values), and Department of Motor Vehicles (DMV information). In the future, MIB Group may insert this information into a blockchain. For example, in the current embodiment depicted in FIG. 2, two notes 44 and 46 indicate that the Medical Information Bureau blockchain 32 includes two nodes of data pertaining to the user. For example, the node 44 may include data indicative of a previously submitted medical questionnaire, while node 46 may include data indicative of lab results, information provided by a doctor, and/or DMV information.

The Medical Records blockchain 34 may include any and/or all pertinent medical records associated with a user. For example, dental records, eye exams, annual checkup reports, treatment reports, etc. may be provided on a user's Health Blockchain 30 (e.g., via the Medical Records blockchain 34). In the depicted embodiment, the user's Medical Records blockchain 34 includes three nodes 48, 50, and 52, which may each represent a submitted medical record.

In some embodiments, a Lab Results blockchain 36 may provide results of a user's lab testing. For example, each time a lab determines results from a lab test for the user, the lab may publish the results to the Lab Results blockchain 36. In the depicted embodiment, four nodes 54, 56, 58, and 60 are on the user's Lab Results blockchain 36, each of the nodes 54, 56, 58, and 60 providing an indication of lab results, such as drug testing results, pregnancy test results, DNA sequencing results, cancer screening results, etc.

The Hospital blockchain 38 may include any pertinent information provided by the user's hospitals. For example, the Hospital blockchain 38 may include patient information, previously provided diagnoses, assigned healthcare personnel, scheduled appointment information, etc. In the depicted embodiment, the Hospital blockchain 38 includes two nodes 62 and 64.

The Pharmacy blockchain 40 may include various data submitted by a Pharmacy. For example, the Pharmacy blockchain 40 may include data indicating previously fulfilled prescriptions, allergy information, etc. In the depicted embodiment, the Pharmacy blockchain includes three nodes 66, 68, and 70, published by one or more pharmacies.

The Department of Insurance blockchain 42 may include information pertaining to insurance policies of the user. For example, the Department of Insurance blockchain 42 may include nodes (e.g., four nodes 72, 74, 76, and 78) indicating current policies held by the user, former and/or current claims by the user, etc.

As may be appreciated, this aggregation of digital data may be quite useful for an automated underwriting process. However, additional data aggregation may result in even more effective automatic underwriting. FIG. 3 is a schematic diagram illustrating a blockchain wallet 90. The blockchain wallet 90 may include an aggregation of blockchains and/or data. In the embodiment depicted in FIG. 3, the blockchain wallet 90 includes an aggregation of the health blockchain 30, with a social media blockchain/data 92, a fitness blockchain/data 94, banking blockchain/data 96, investment blockchain/data 98, digital currency blockchain/data 100, mortgage blockchain/data 102, and digital card blockchain/data 104.

The social media blockchain/data 92 may provide an indication of social media posts, pictures, statistics, etc. that are associated with a user. For example, oftentimes information may be gleaned from social media posts regarding an amount of physical activity a user partakes in. Further, such posts may indicate eating habits, sleeping habits, drinking habits, and/or smoking habits. Additionally, statistics, such as relationship statistics (e.g., single vs. married, etc.) may be obtained via the social media blockchain/data 92.

A fitness blockchain/data 94 may provide a detailed indication of fitness of a user. For example, heartrate, physical activity, and other vital statistics may be accumulated by electronic wearables of the user. This information may be posted to the fitness blockchain/data 94 for subsequent use in the blockchain wallet 90.

The banking blockchain/data 96 may provide an indication of banking information for the user. For example, the banking blockchain/data 96 may provide a credit-worthiness indication or other information relevant to personalized quotes.

The investments blockchain/data 98 may provide an indication of current investments, retirement accounts, etc. Further, beneficiary information for retirement accounts may be gleaned from the investments blockchain/data 98.

The digital currency blockchain/data 100 may provide an indication of digital currency transactions and/or a retained amount of digital currency of the user. This information may be used to determine credit-worthiness of the user along with a risk associated with the user.

The mortgage blockchain/data 102 may provide an indication of current mortgages of the user. This data may improve service offerings. For example, during the service application process, additional service offerings may be provided to the user (e.g., homeowner's and/or landlord's insurance policies).

The digital cards blockchain/data 104 may provide information relating to the user's digital payment methods, memberships, etc. This information may be readily available and used to provide discount options (e.g., based upon membership or having multiple products with the same institution). For example, in some embodiments, a discount may be provided when a user has a membership with a qualifying institution. Further, digital cards can replace physical cards, keeping user from having to remember this information and avoid having them lost or stolen; user can just pull it up on their digital blockchain wallet.

Figure 4:
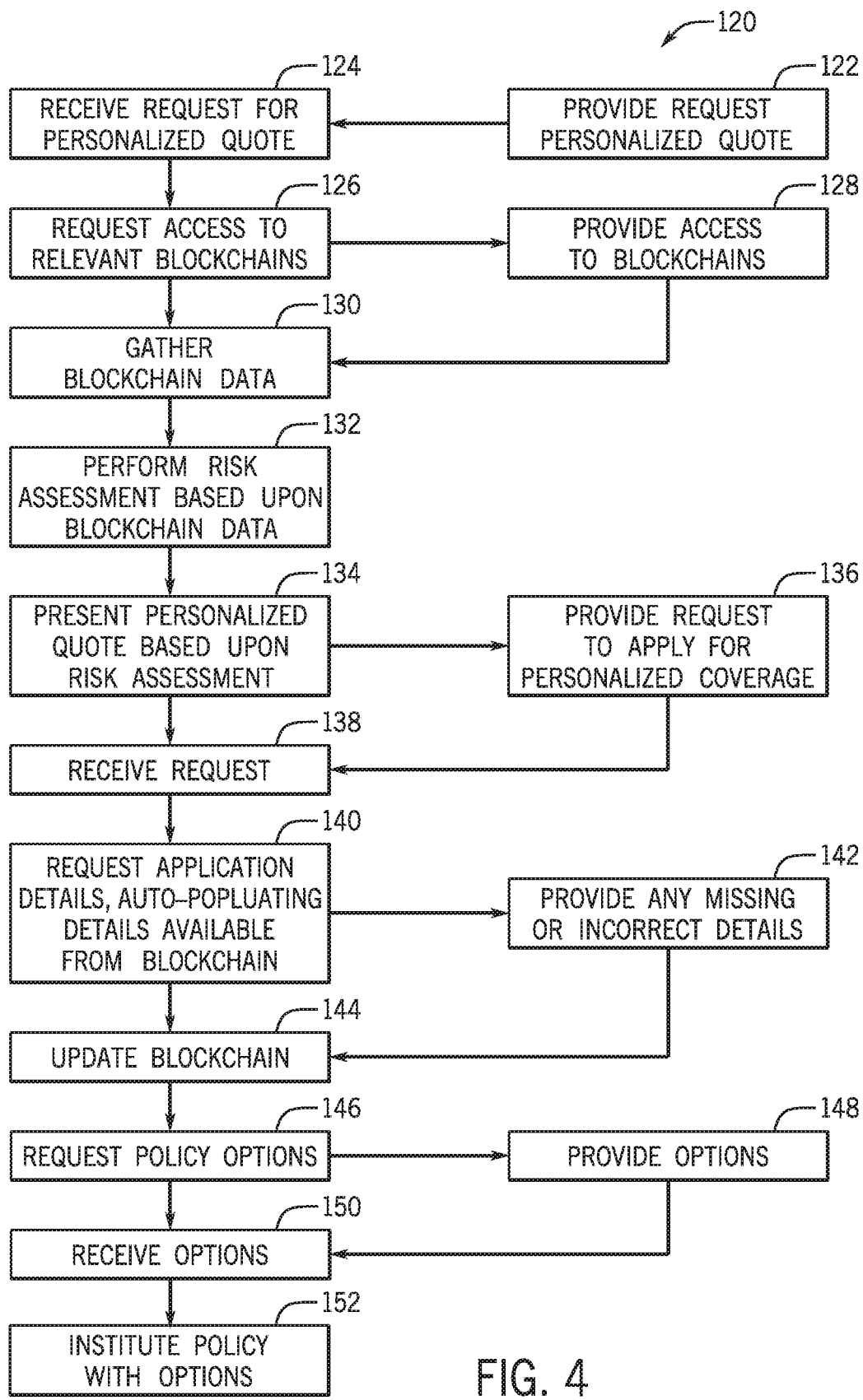
FIG. 4 is a flowchart, illustrating a process for automated underwriting and service acquisition based upon blockchain data, in accordance with an embodiment.

Turning now to the underwriting and automated service acquisition, FIG. 4 is a flowchart, illustrating a process 120 for automated underwriting and service acquisition based upon blockchain data, in accordance with an embodiment. As may be appreciated, portions of the process 120 may be optional. Further, while the discussion uses example graphical user interfaces (GUI) to demonstrate the process 120, alternative GUIs may be used in performance of the process 120.

Figure 5:
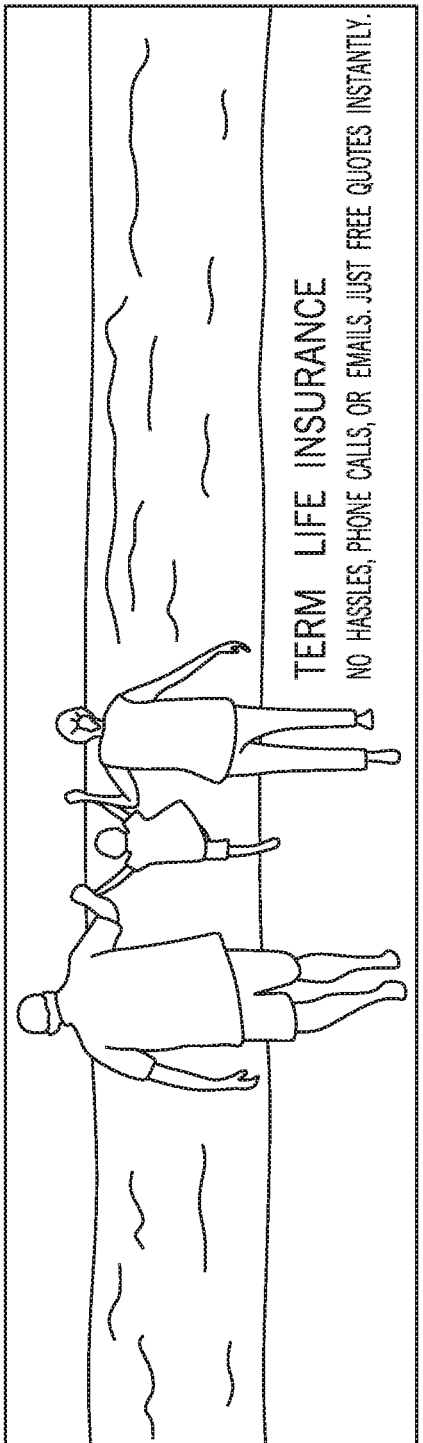
FIG. 5 is a schematic diagram, illustrating a graphical user interface (GUI) for providing a non-personalized service quote along with a mechanism to request a personalized service quote, in accordance with an embodiment.

The process 120 begins by receiving a request for personalized quote (block 122). FIG. 5 is a schematic diagram, illustrating a graphical user interface (GUI) for providing a non-personalized service quote along with a mechanism to request a personalized service quote, in accordance with an embodiment. In the embodiment of FIG. 5, non-personalized quotes 172A, 172B, and 172C are provided for a set of service providers A, B, and C, respectively. The non-personalized quotes 172A, 172B, and 172C take into account very few factors and may be adjusted significantly after additional factors specific to the user are considered. For example, the non-personalized quotes 172A, 172B, and 172C may merely take into account the terms and average the monthly premium across the plans that the service provider provides with the same terms. In some embodiments, the non-personalized quote may include basic information, such as age and gender, while leaving out many details of the user that are pertinent to an actual quote. To provide a request for a personalized quote (block 122), the user may click one of the personalized quote buttons 174A, 174B, or 174C, pertaining to the service provider A, B, or C that is desired.

Returning to the process 120, the company A, B, or C (or the company's agent) may receive the request for personalized quote (block 124). For example, assuming that the user selected button 174B, a request for personalized quote may be received at a service provider's server (or at service provider's agent's server). The request may include identifying information regarding the user, terms desired by the user, etc.

After the request is received, the company and/or the company's agent may request, via the server, access to relevant blockchains that contain data relevant to the personalized quote (block 126). For example, FIG. 6 is a schematic diagram of a graphical user interface 190 for permitting access to components of a blockchain wallet 90 for underwriting purposes, in accordance with an embodiment. As previously mentioned, the blockchain wallet 90 may include an aggregation of the health blockchain 30, with a social media blockchain/data 92, a fitness blockchain/data 94, banking blockchain/data 96, investment blockchain/data 98, digital currency blockchain/data 100, mortgage blockchain/data 102, and digital card blockchain/data 104. The company may utilize data from all or a subset of these blockchains/data. Based upon the blockchains/data that are used, the GUI 190 may populate checkboxes (or other selection indicators) at blockchains/data that should be accessed for the personalized quote. For example, in the current embodiment, rows 192, 202, and 206 are pre-selected, indicating that the service provider (e.g., CO2) is requesting access to an identify of the user, the social media blockchain/data 92, and the health blockchain 30. The unselected items in rows 194, 196, 198, 200, and 204 indicate that these blockchains/data are not necessary for the personalized quote and that no access is being requested for these blockchains/data. The user may decline to provide access to the selected blockchains/data by clicking the decline button 208. However, when declining access to the blockchains/data, the automated underwriting and acquisition of services is halted, instead sending the user to the manual process of the user directly providing relevant data to the service provider. To approve access to the selected blockchains/data, the user may select the agree button 210, which provides access to the blockchains/data (block 128 of FIG. 4).

Figure 7:
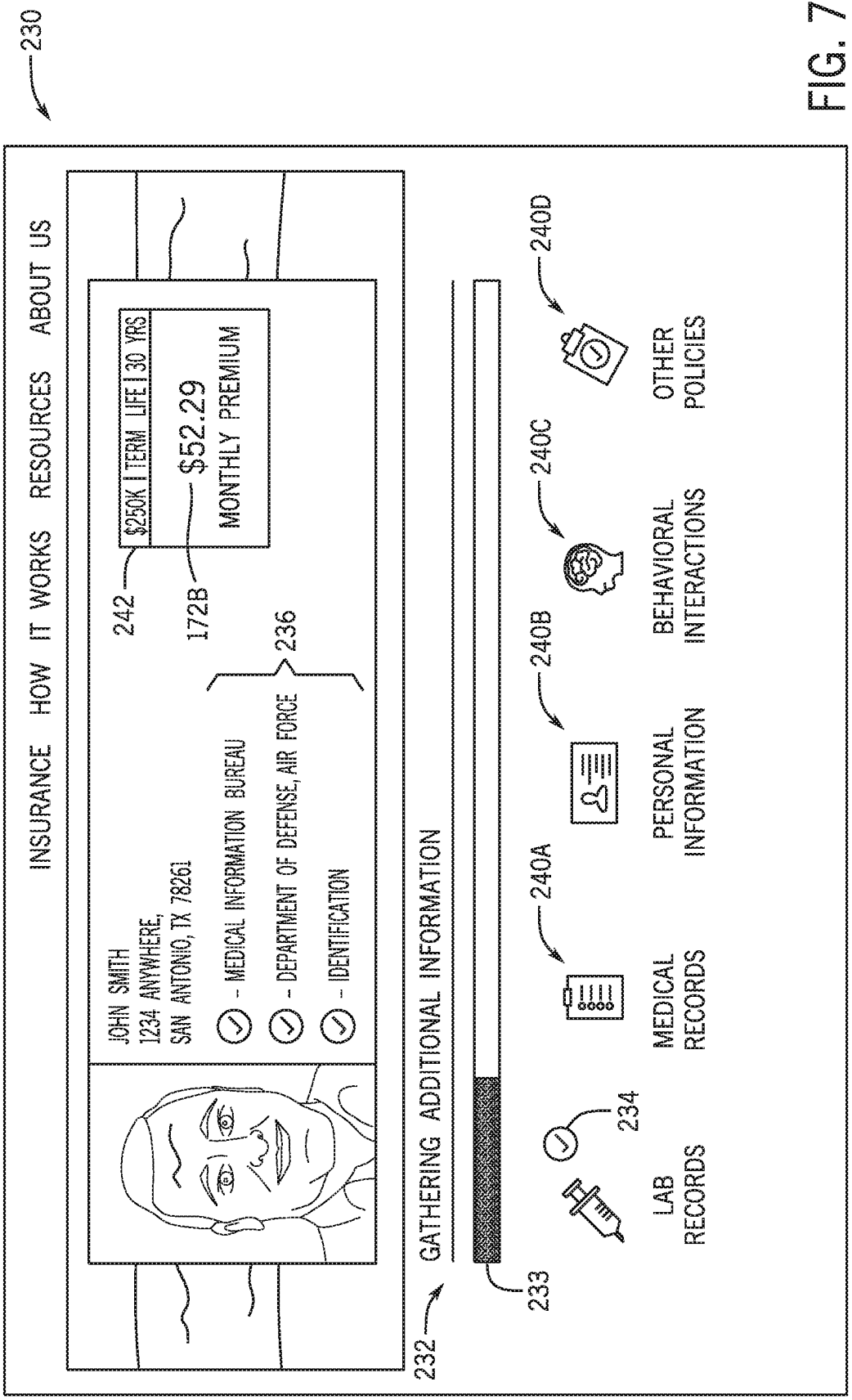
FIG. 7 is a schematic diagram, illustrating a graphical user interface (GUI) for providing a progress indicator during acquisition of relevant blockchain data for a personalized service quote, in accordance with an embodiment.

Returning to the process 120 of FIG. 4, once access is provided, the blockchain data is gathered (block 130). FIG. 7 is a schematic diagram, illustrating a graphical user interface (GUI) 230 for providing a progress indicator 232 during acquisition of relevant blockchain data for a personalized service quote, in accordance with an embodiment.

Certain base data 236 that is used to access the additional information may be provided in a different section or in the same section as the information that is being gathered. In the current embodiment, Medical Information Bureau information, Department of Defense information, and Identification information may be used to access certain blockchains/data. Accordingly, this base data is collected first and presented in a separate area of the GUI 230. Once the base data 236 is acquired, the blockchain/data may be acquired.

As illustrated, the progress indicator provides an indication of the particular blockchain information that is being retrieved (e.g., via the status bar 233). In some embodiments, once particular blockchains/data are retrieved, an indicator of the completed retrieval may be provided (e.g., checkmark icon 234, which is displayed after lab record data is retrieved).

In the depicted example, the lab record acquisition is complete, but medical records 240A, personal information 240B, behavioral interactions 240C (e.g., social media posts indicating behaviors, etc.), and other policy information 240D (e.g., other policies held by the user) have yet to be acquired. As may be appreciated, the non-personalized quote 172B is presented, as the data useful for determining the quote has not been completely acquired or analyzed. Additionally, the terms 242 of the non-personalized quote 172B are also provided.

Returning to process 120 of FIG. 4, once the blockchain/data is gathered (either partially or fully), the risk assessment analysis may be performed using the gathered blockchain/data (block 132). For example, if the behavioral interactions 240C indicate that the user smokes (e.g., based upon posts with cigarettes in the user's post) and/or drinks heavily (e.g., based upon posts with alcoholic beverages), the insurance risk associated with the user may increase. Similarly, if medical records indicate relatively serious illnesses or frequent medical procedures, the insurance risk associated with the user may increase.

Figure 8:
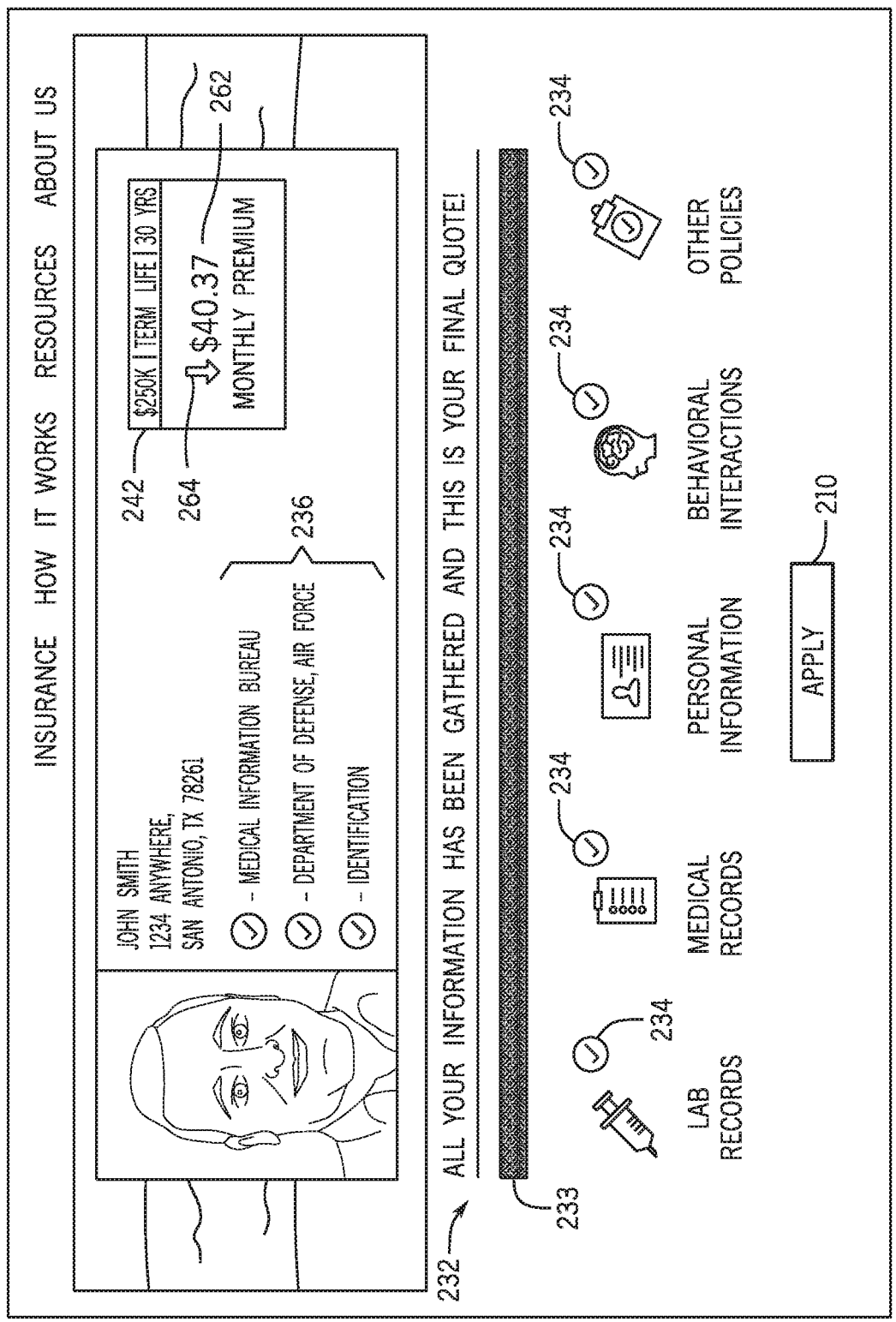
FIG. 8 is a schematic diagram, illustrating a graphical user interface (GUI) for providing a personalized service quote along with a mechanism to request application for the personalized service quote, in accordance with an embodiment.

Once the risk assessment is performed a personalized quote may be determined and presented, based upon the risk assessment (block 134). FIG. 8 is a schematic diagram, illustrating a graphical user interface (GUI) 260 for providing a personalized service quote 262 along with a mechanism to request application for the personalized service quote, in accordance with an embodiment. As illustrated in FIG. 8, the checkmark icon 234 is presented near each of the blockchains/data, indicating that the acquisition of all of the blockchain/data has been completed. Further the status bar 233 indicates that each of the blockchains/data have been acquired. Based upon analysis of the acquired blockchains/data, the personalized risk assessment for John Smith indicates a lower risk level than the average risk level used in the non-personalized quote 172B. Accordingly, the personalized quote is reduced in conjunction with this reduced risk. Further, a decrease indicator 264 is presented. Had John Smith's personalized risk level been higher than the average risk level used by the non-personal quote, the personalized quote 262 would have increased and an increase indicator would have optionally been presented.

If the user desires to apply for the service after receiving the personalized quote, the user may provide a request to apply for the service associated with the personalized quote (block 136 of FIG. 4). For example, in FIG. 8, the user may select the "APPLY" button 264.

Once the request is received (block 138), additional application details may be requested (block 140). Details that have already been gathered (e.g., via the blockchain/data gathering of block 130) may be auto-populated, enabling the user to modify any incorrect information. FIG. 9 is a schematic diagram, illustrating a graphical user interface (GUI) 290 for providing an auto-populated application for the personalized service, in accordance with an embodiment. As illustrated, when GUI 290 is rendered, information known to the system (e.g., via gathering of blockchain/data) is auto-populated. In the current embodiment, each of the fields in the application verification section 292 are prepopulated, as the information was obtained during the blockchain/data gathering (block 130). Additional service offerings 294 may be provided to users who qualify, based upon the gathered blockchain/data. For example, for creditworthy users, credit card offers 294A may be provided. For users meeting investment requirement, an investments option 294B may be provided. For users that meet banking requirements, banking and savings options 294C may be provided. Additionally, home options 294D and auto options 294E may be provided. The user may provide any missing or incorrect details (block 142 of FIG. 4) and confirm the selections (e.g., via the "YES, THIS IS CORRECT" button 296. In some embodiments, when incorrect details are pinpointed and corrected by the user, the service may update the blockchain (block 144 of FIG. 4).

The service may request policy options from the user (block 146). FIG. 10 is a schematic diagram, illustrating a graphical user interface (GUI) 310 for providing personalized service options, in accordance with an embodiment. The policy benefits section 312 provide policy benefits available to the user. For example, John's plan includes an accelerated death benefit 314. In addition, personalized benefits may be provided based upon gathered blockchain/data. For example, the gathered blockchain/data may indicate that John is a member of military (e.g., Air Force). Accordingly, Military Severe Injury Benefits 316 and Military Future Insurability Benefits 318 may be provided as a customized benefit for John.

The policy options section 320 provides policy options to John. For example, a policy option may include additional child protection plan coverage options 322. However, in the current example, the system may be aware that John does not have children (based upon gathered blockchains/data) and may default option 322 to NO and/or provide an indication 324 that no children are eligible for coverage.

The beneficiaries section 326 enables the user to select beneficiaries for the service. In some instances this information may be pre-populated with spouse information, when this system is aware of a spouse (e.g., from the gathered blockchain/data). In some embodiments, this pre-population of the spouse may be used specifically in jurisdictions where spousal rights must be granted or explicitly waived by the spouse.

The billing section 328 enables the user to select a billing method for the policy. In some embodiments, digital card information from the gathered blockchain/data may be pre-populated. Once the user is finished completing options, the options may be provided to the service (block 148).

Figure 11:
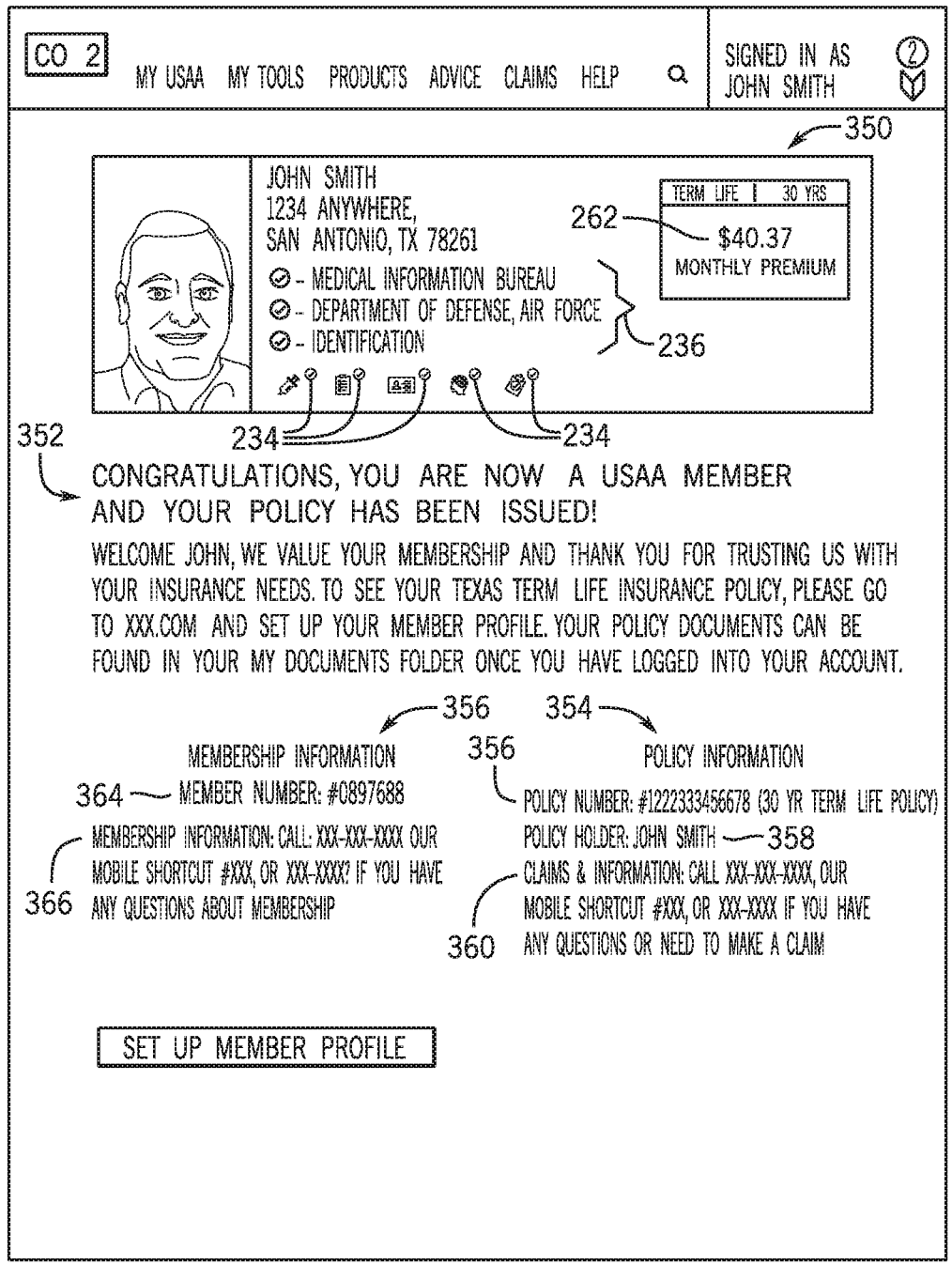
FIG. 11 is a schematic diagram, illustrating a graphical user interface (GUI) for providing a confirmation regarding acquisition of the personalized service with selected service options, in accordance with an embodiment.

Once the options are received (block 150), the policy is implemented with the options (block 152). FIG. 11 is a schematic diagram, illustrating a graphical user interface (GUI) 350 for providing a confirmation 352 regarding acquisition of the personalized service with selected service options, in accordance with an embodiment. A policy information section 354 may provide relevant policy information, such as policy number 356, the policy holder 358 and/or claims and information support 360. Further, implementation of the policy may result in membership in an organization in some instances. Membership information 362 may provide membership information, such as member number 364 and member information support 366.

As may be appreciated, use of blockchains/data may provide new benefits for underwriting and service acquisition not seen in traditional human transactions. For example, by using electronic data, errors may be reduced, while being able to process significantly more data in significantly less time. Further, additional new data sources (e.g., social media posts) may provide additional information that may be useful for generating a personalized quote for services.

While only certain features of the disclosure have been illustrated and described herein, many modifications and changes will occur to those skilled in the art. It is, therefore, to be understood that the appended claims are intended to cover all such modifications and changes as fall within the true spirit of the invention.

The invention claimed is:

1. A tangible, non-transitory, machine-readable medium, comprising machine-readable instructions that, when executed by at least one processor, cause the processor to:

receive a request, via a website, for a personalized quote for a product;

identify a requestor that provided the request;

gather blockchain data from a plurality of independent blockchains into gathered blockchain data of a blockchain wallet associated with the requestor, wherein the blockchain data comprises data pertinent to the personalized quote;

auto-populate at least one of a set of application fields of the website with at least a portion of the gathered blockchain data of the blockchain wallet;

receive, via the website, modifications to the at least one of the set of application fields that were auto-populated;

provide an update to a particular blockchain of the plurality of independent blockchains that sourced the blockchain data associated with the modifications to update the particular blockchain based upon the modifications;

determine the personalized quote based at least in part upon the gathered blockchain data of the blockchain wallet; and present the personalized quote via the web site.

2. The machine-readable medium of claim 1, comprising instructions that cause the processor to:

request access from the user to the blockchain data, via the website; and upon receiving the access, gather the blockchain data.

3. The machine-readable medium of claim 1, comprising instructions that cause the processor to:

present, via the website, an application form, comprising the set of application fields for applying for the product.

4. The machine-readable medium of claim 1, comprising instructions that cause the processor to:

receive, via the web site, additions, deletions, or any combination thereof to at least one of the set of application fields; and update the blockchain data based at least in part upon the additions, deletions, or any combination thereof.

5. The machine-readable medium of claim 1, comprising instructions that cause the processor to:

present, via the website, available options for the product.

6. The machine-readable medium of claim 5, comprising instructions that cause the processor to:

auto-populate a choice of at least one of the available options based at least in part upon the blockchain data.

7. The machine-readable medium of claim 5, comprising instructions that cause the processor to:

provide at least one of the available options based at least in part upon the blockchain data.

8. The machine-readable medium of claim 1, wherein the blockchain data comprises data from a blockchain wallet, the blockchain wallet comprising an aggregation of a health blockchain associated with the requestor and at least one of a social media blockchain, a fitness blockchain, a banking blockchain, an investments blockchain, a digital currency blockchain, a mortgage blockchain, and a digital cards blockchain.

9. The machine-readable medium of claim 1, comprising instructions that cause the processor to:

present a progress indicator during gathering of the blockchain data.

10. The machine-readable medium of claim 9, wherein the progress indicator provides an indication of blockchain data that has been acquired and blockchain data that remains to be acquired.

11. The machine-readable medium of claim 1, comprising instructions that cause the processor to:

receive, via the website, an application request for the product, based at least in part upon the personalized quote;

upon receiving the application request, automatically issue the product to the requestor, based at least in part upon the personalized quote.

12. The machine-readable medium of claim 1, comprising instructions that cause the processor to:

access social media blockchain from the blockchain wallet;

retrieve one or more images associated with the requester from the social media blockchain;

determine a risk factor associated with the requestor based on one or more indications of a behavioral interaction from the one or more images;

perform a risk assessment analysis using the risk factor; and adjust the personalized quote based on the risk assessment analysis.

13. The machine-readable medium of claim 1, comprising instructions that cause the processor to:

prior to determining the personalized quote, present a graphical user interface (GUI) to the requestor, wherein the GUI comprises a list of the plurality of independent blockchains;

populate the GUI with a selection indicator indicating that the blockchain data of the particular blockchain from the plurality of independent blockchains is accessed for determining the personalized quote; and receive a selection from the requestor grant or revoke access to the blockchain data of the particular blockchain.

14. A computer system, comprising:

a processor; and an electronic display;

wherein the computer system is configured to:

receive a request, via a website displayed on the electronic display, the request for a personalized quote for a product;

identify, via the processor, a requestor that provided the request;

gather, via the processor, blockchain data from a plurality of independent blockchains into gathered blockchain data of a blockchain wallet associated with the requestor, wherein the blockchain data comprises data pertinent to the personalized quote;

auto-populate, via the processor, at least one of a set of application fields of the website with at least a portion of the gathered blockchain data of the blockchain wallet;

receive, via the website, modifications to the at least one of the set of application fields that were auto-populated;

provide, via the processor, an update to a particular blockchain of the plurality of independent blockchains that sourced the blockchain data associated with the modifications to update the particular blockchain based upon the modifications;

determine, via the processor, the personalized quote based at least in part upon the gathered blockchain data of the blockchain wallet; and present the personalized quote via the website on the electronic display.

15. The computer system of claim 14, configured to:

receive, via the website, an application request for the product, based at least in part upon the personalized quote;

upon receiving the application request, automatically issue the product to the requestor, based at least in part upon the personalized quote.

16. The computer system of claim 14, configured to:
present, via the website, an application form, comprising the set of application fields for applying for the product;
receive, via the website, additions, deletions, or any combination thereof to at least one of the set of application fields; and
update the blockchain data based at least in part upon the additions, deletions, or any combination thereof.

17. A computer-implemented method, comprising:
receiving a request, via a website, for a personalized quote for a product;
identifying a requestor that provided the request;
gathering blockchain data from a plurality of independent blockchains into gathered blockchain data of a blockchain wallet associated with the requestor, wherein the blockchain data comprises data pertinent to the personalized quote;
auto-populating at least one of a set of application fields of the website with at least a portion of the gathered blockchain data of the blockchain wallet;
receiving, via the website, modifications to the at least one of the set of application fields that were auto-populated;
providing an update to a particular blockchain of the plurality of independent blockchains that sourced the blockchain data associated with the modifications to update the particular blockchain based upon the modifications;
determining the personalized quote based at least in part upon the gathered blockchain data of the blockchain wallet; and
presenting the personalized quote via the website.

18. The computer-implemented method of claim 17, wherein the blockchain data comprises a health blockchain.

19. The computer-implemented method of claim 18, wherein the health blockchain comprises:
nodes of a Medical Information Bureau blockchain, nodes of a Medical Records blockchain, nodes of a Lab Results blockchain, nodes of a Hospital blockchain, nodes of a Pharmacy blockchain, nodes of a Department of Insurance blockchain, or any combination thereof.

20. The computer-implemented method of claim 19, wherein the blockchain data comprises data from at least one of a social media blockchain, a fitness blockchain, a banking blockchain, an investments blockchain, a digital currency blockchain, a mortgage blockchain, and a digital cards blockchain.

\* \* \* \* \*